United States Patent [19]

Nakamura et al.

[11] Patent Number: 5,013,159

[45] Date of Patent: May 7, 1991

[54] THERMAL ANALYSIS APPARATUS

[75] Inventors: Nobutaka Nakamura; Haruo Takeda; Masafumi Take, all of Tokyo, Japan

[73] Assignee: Seiko Instruments, Inc., Tokyo, Japan

[21] Appl. No.: 420,311

[22] Filed: Oct. 12, 1989

[30] Foreign Application Priority Data

Oct. 13, 1988 [JP] Japan ................. 63-257992

[51] Int. Cl.$^5$ ............. G01N 25/00; G01K 1/20
[52] U.S. Cl. ................. 374/12; 62/148; 236/91 A; 374/16; 392/497
[58] Field of Search ............ 374/16, 54; 73/28; 219/331, 201; 62/64, 149, 148; 236/91 A

[56] References Cited

U.S. PATENT DOCUMENTS

| 3,195,620 | 7/1965 | Steinhardt, Jr. | 219/331 X |
| 3,305,000 | 2/1967 | Bullen et al. | 73/23.1 X |
| 4,107,937 | 8/1978 | Chmiel | 62/64 |
| 4,117,713 | 10/1978 | Phillips et al. | 73/28 X |
| 4,314,459 | 2/1982 | Rivoire | 62/51.1 |

Primary Examiner—Daniel M. Yasich
Attorney, Agent, or Firm—Spensley Horn Jubas & Lubitz

[57] ABSTRACT

Apparatus for controlling the temperature of a sample in a thermal analysis system according to a temperature-control program in order to facilitate the production of rising and falling temperatures. The apparatus includes a first heater, a thermally insulating container having an opening and containing a mass of liquified coolant, a coolant vapor flow pipe, a sample chamber for containing the sample, a second heater, a sample chamber temperature detector, a temperature-control program setting circuit, a first power supply regulator and a second power supply regulator. The first heater is disposed within the liquified coolant in the container and is operated according to a desired temperature-control program set in the setting circuit to vaporize the liquified coolant so that the vaporized coolant is introduced through the pipe and into the sample chamber to cool the interior of the chamber, while the interior of the chamber is heated by the second heater to thereby control the production of rising and falling temperatures in the sample chamber.

3 Claims, 1 Drawing Sheet

THERMAL ANALYSIS APPARATUS

BACKGROUND OF THE INVENTION

The present invention relates to improvements in the control of heating and cooling measurements of a thermal analysis apparatus used for analyzing temperature dependencies of physical characteristics of materials.

There are various types of conventional temperature control systems or methods, such as those using the following mechanisms: (1) while circulating liquified coolant around a sample chamber to cool the same, the sample chamber is heated by means of a heater disposed within the sample chamber to thereby control the sample chamber temperature; (2) while introducing liquified coolant directly into a sample chamber to cool the same, the sample chamber is heated by means of a heater disposed around the sample chamber to thereby control the sample chamber temperature; and (3) while introducing into a sample chamber gas cooled by liquified coolant to cool the sample chamber, the sample chamber is heated by means of a heater disposed within the sample chamber to thereby control the sample chamber temperature.

While, with the above-mentioned approaches, the heating of the sample chamber by means of the heater does not cause any problem in any of the conventional systems, there have been the following problems with respect to the cooling of the sample chamber. With regard to conventional system (1), since the interior of the sample chamber is not directly cooled but the outer periphery thereof is cooled, the cooling capacity of the coolant source is not sufficient when the sample chamber is not completely insulated, thereby considerably restricting the design of the thermal analysis device. With regard to conventional system (2), while sufficient cooling capacity can be obtained, the balance between cooling and heating by means of the heaters is difficult to control, thereby causing the drawback that the temperature control of the sample chamber cannot be accurately effected. With regard to conventional system (3), since the utilized gas is required to have a boiling point lower than that of the liquified coolant, costly materials are necessary. Moreover, moisture contained in the gas freezes to cause problems such as blockage of gas flow paths.

SUMMARY OF THE INVENTION

A broad object of the present invention is to provide thermal analysis apparatus which avoid the above-noted drawbacks.

A more specific object of the present invention is to eliminate the above-noted drawbacks of the prior art.

The above and other objects are achieved, according to the invention, by an analysis apparatus composed of: a first heater, a thermally insulating container provided with which the first heater is disposed, the container having an opening at its top and containing a liquified coolant, a pipe connected to the opening of the thermally insulating container for passing vaporized coolant, a sample chamber connected to the pipe for receiving coolant and having an exhaust opening for discharging the vaporized coolant, a second heater disposed within the sample chamber for heating the interior of the sample chamber, a temperature detector for measuring the temperature inside the sample chamber, a temperature-control program setting circuit for setting a desired temperature-control program and outputting a corresponding temperature-control signal, a first power supply regulator connected to the temperature-control program setting circuit and to the first heater for regulating the power supplied to the first heater according to the temperature-control signal, and a second power supply regulator connected to the temperature-control program setting circuit, the temperature detector and the second heater for regulating the power supplied to the second heater according to the difference between the temperature-control signal and a detection signal from the temperature detector.

When the output level of the temperature-control program setting circuit is lower than room temperature, the first power supply regulator supplies electric power to the first heater to generate in the heater thermal energy effective to vaporize a corresponding amount of the liquified coolant inside the insulating container. The vaporized coolant is introduced through the vaporized coolant pipe into the sample chamber to cool the sample chamber. In this operation, the lower the temperature indicated by the output temperature-control signal of the temperature-control program setting circuit, the greater the power supplied to the first heater so as to raise the cooling capacity of the sample chamber. Further, at the same time, the second power supply regulator operates according to the difference between the output signal of the temperature-control program setting circuit and the output signal of the temperature detector to supply electric power to the second heater so as to effect temperature control in a manner to reduce the difference between the output signals. Consequently, the sample chamber of the analysis apparatus is temperature controlled according to the temperature control program to thereby achieve the object of the present invention.

DESCRIPTION OF THE PREFERRED EMBODIMENTS

Figure 1:
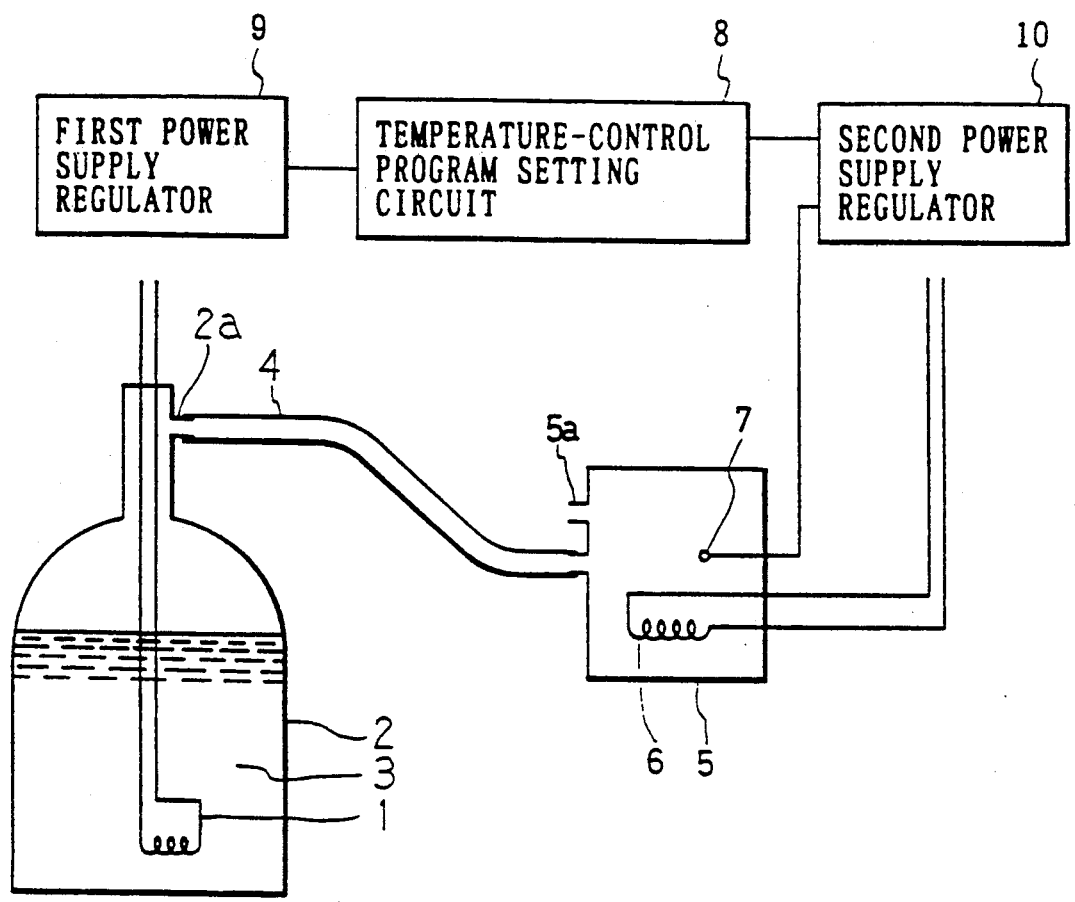
FIG. 1 is a schematic diagram of one embodiment of the present invention.

One embodiment of the present invention is described in detail hereinafter with reference to FIGS. 1 and 2 of the drawings. FIG. 1 shows a first heater 1 disposed inside a thermally insulating container 2 having an opening at its top. The insulating container 2 is filled with a liquified coolant 3 in the form of a liquid nitrogen. A vapor removal pipe 4 has one end connected to an opening 2a near the top of insulating container 2, and is connected at its other end to a sample chamber 5 which is formed to have a gas exhaust opening 5a. Further, a second heater 6 and a temperature detector 7 are provided inside sample chamber 5.

A temperature-control program setting circuit 8 is provided to set a temperature-control program and operates to output a temperature-control signal according to the set temperature-control program. A first power supply regulator 9 is connected to the temperature-control program setting circuit 8 and to the first heater 1. The first power supply regulator 9 operates according to the output from the temperature-control program setting circuit 8 to regulate electric power supplied to the first heater 1.

Further, a second power supply regulator 10 is connected to the temperature-control program setting circuit 8, the temperature detector 7 and the second heater 6 and operates according to the difference between the output signal of the temperature-control program setting circuit and the output signal of the temperature detector 7 to regulate electric power supplied to the second heater 6 so as to maintain in chamber 5 the temperature set by circuit 8.

In operation of the thermal analysis apparatus according to the present invention, at first a desired temperature-control program or profile is set in the temperature-control program setting circuit 8. Next, when operating the temperature-control program setting circuit 8, it sequentially and continuously outputs a desired temperature-control signal according to the program. During this operation, according to the latter-described process based on the temperature-control program, necessary electric power is supplied to the first heater 1 through the first power supply regulator 9. The electric power supplied to the first heater 1 is immediately converted into vaporized energy for surrounding liquid nitrogen to vaporize a given amount of the liquid nitrogen 3 corresponding to the supplied electric power. The vaporized liquid nitrogen comprises cooled nitrogen gas having a temperature close to the boiling temperature of the liquid nitrogen ($-196°$ C.). The generated vapor containing nitrogen gas is fed through the opening 2a of the insulating container 2 and the vaporized coolant pipe 4 to the sample chamber 5. The nitrogen gas cools the sample chamber 5 and then is discharged out of chamber 5 via the gas exhaust opening 5a.

A detailed description will now be given for the operation of the first power supply regulator 9. The input/output relation thereof is set as follows. Namely, the output in the form of power is related to the input in the form of the temperature-control signal according to the following equation:

$$P = \alpha(Tp) + \beta \frac{dTp}{dt} \quad (1)$$

where
P: electric power supplied to heater 1;
Tp: programmed temperature;
α: supply voltage function in terms of the programmed temperature;
t: time $\frac{dTp}{dt}$ : rate of programmed temperature change;

β: a constant

The above-mentioned function α(Tp) is predetermined experimentally as follows: A constant electric power of, for example, 100 W is supplied to the first heater 1, and, after 30 minutes, the output temperature of the temperature detector 7 reads, for instance $-90°$ C. Next, in similar manner, with a different power level supplied to heater 1, the output temperature is again read from the temperature detector 7.

Figure 2:
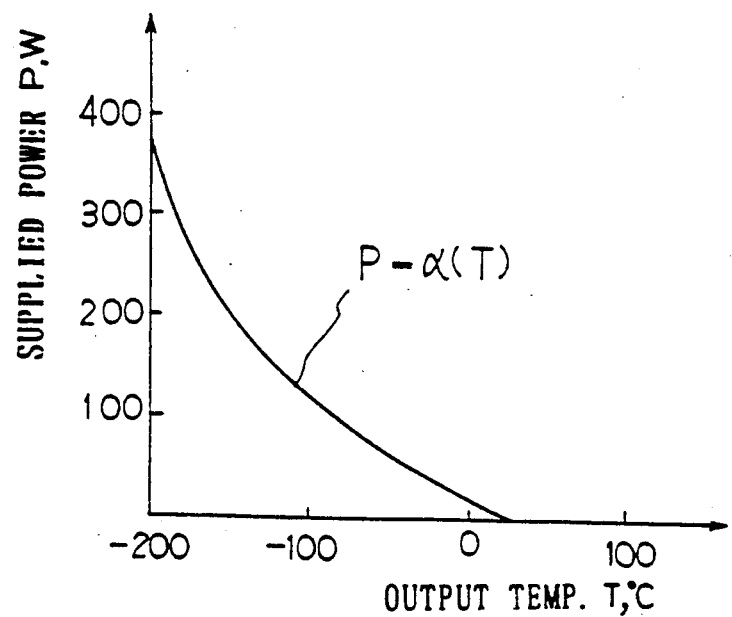
FIG. 2 is a diagram showing an operating characteristic of the apparatus.

The relation between the output temperature and the supply power for various power levels is plotted as shown in FIG. 2 to thereby obtain a value for function α. As described, by determining the particular form of the function α(Tp), according to the first term of equation (1), when setting a given constant value below room temperature as the programmed temperature Tp to work the inventive analysis apparatus, the first power supply regulator 9 and the first heater 1 are accordingly operated to decrease the temperature in the sample chamber 5 to the temperature Tp set by the temperature-control program after 30 minutes.

Further, by setting a negative value to the term β which is the coefficient of the second term of equation (1), the cooling capacity can be lowered in a stage of the temperature-control program when the temperature is rising and can be boosted in a state of the temperature-control program when the temperature is falling to thereby effect ideal cooling control.

In turn, a detailed description is next given of the operation of the second power supply regulator 10. The second power supply regulator 10 supplies to the second heater 6 a specific electric power which is obtained by effecting a well known PID (proportion, integration and differentiation) control processing with respect to the temperature difference signal which is the output difference between the temperature-control program setting circuit 8 and the temperature detector 7, to thereby accurately temperature-control the sample chamber 5 according to the temperature-control program set in the temperature-control program setting circuit 8. Moreover, since the temperature control of the sample chamber 5 by means of the second power supply regulator 10 is carried out continuously without regard to whether the first power supply regulator 9 is in operation or not, accurate temperature-control can be effected in a wide range from low to high temperatures.

As described above, according to the present invention, since the cooling control of the sample chamber by means of the first power supply regulator and the accurate or fine temperature control of the sample chamber by means of the second power supply regulator can be combined with each other in balanced relation, there is achieved the advantage that the temperature of the sample chamber, which determines the temperature of a sample in the thermal analysis apparatus, can be easily and precisely controlled over a range from a lower temperature close to the liquified coolant temperature below the room temperature to a higher temperature of about 700° C. Moreover, since a suitable amount of vaporized liquid coolant can be controllably introduced into the sample chamber, a reduction in operating cost can be realized. In view of the high cooling capacity, design of the analysis apparatus is not restricted unduly.

Circuit 8 can be of an known type used in conventional thermal analysis apparatus, while regulators 9 and 10 can be constructed in a manner conventional for such regulators, using the specific relations set forth above.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A thermal analysis apparatus comprising:

a first electrically operated heater;

a thermal insulating container in which said first heater is disposed, said container having a top provided with a coolant outlet opening and containing a mass of liquified coolant;

a sample chamber having a coolant inlet opening and a gas outlet opening;

a vapor flow pipe connected between said coolant outlet opening and said coolant inlet opening for conducting coolant vapor from said container to said chamber;

a second electrically operated heater disposed in said chamber to heat the interior of said chamber;

temperature detecting means disposed for detecting the actual temperature within said sample chamber and providing an output signal representative of that temperature;

a temperature control program setting circuit for producing a control signal representing a desired temperature;

a first power supply regulator connected between said temperature control program setting circuit and said first heater and responsive to the control signal produced by said temperature control program setting circuit for regulating the electrical power supplied to said first heater in a manner to cause coolant in said container to be vaporized at a selected rate and to flow through said pipe into said sample chamber in order to cool the interior of said sample chamber; and a second power supply regulator connected to said temperature control program setting circuit, said temperature detecting means and said second heater for receiving said control signal and said output signal and regulating the electrical power supplied to said second heater as a function of the difference between the desired temperature and the actual temperature within said chamber in order to heat the interior of said chamber to the desired temperature.

2. Apparatus as defined in claim 1 wherein the signal supplied by said setting device to said second regulator varies in a manner to cause the temperature in said chamber to vary in a controlled manner.

3. Apparatus as defined in claim 2 wherein the liquid coolant is maintained at a temperature below ambient temperature.

* * * * *